United States Patent [19]

Sakamoto et al.

[11] Patent Number: 5,504,243

[45] Date of Patent: Apr. 2, 1996

[54] METHOD FOR INHIBITING POLYMERIZATION OF (METH) ACRYLIC ACID AND ESTERS THEREOF

[75] Inventors: Kazuhiko Sakamoto; Takahiro Takeda; Masatoshi Ueoka; Yoji Akazawa; Masao Baba, all of Himeji, Japan

[73] Assignee: Nippon Shokubai Co., Ltd., Osaka, Japan

[21] Appl. No.: 444,869

[22] Filed: May 19, 1995

[30] Foreign Application Priority Data

Jun. 2, 1994 [JP] Japan .................... 6-121496

[51] Int. Cl.⁶ .................................. C07C 69/52
[52] U.S. Cl. ......................... 560/205; 562/598
[58] Field of Search ............... 560/205; 562/598

[56] References Cited

U.S. PATENT DOCUMENTS

| | | |
|---|---|---|
| 4,021,310 | 5/1977 | Shimizu et al. . |
| 4,127,603 | 11/1978 | Bljumberg et al. ............... 562/533 |
| 4,210,493 | 7/1980 | Stewart et al. . |
| 5,322,960 | 6/1994 | Sakamoto et al. ............... 560/205 |

FOREIGN PATENT DOCUMENTS

| | | |
|---|---|---|
| 0178168 | 4/1986 | European Pat. Off. . |
| 0371748 | 6/1990 | European Pat. Off. . |
| 0485169 | 5/1992 | European Pat. Off. . |
| 1064845 | 4/1967 | United Kingdom . |
| 1127127 | 9/1968 | United Kingdom . |
| 1265419 | 3/1972 | United Kingdom . |

*Primary Examiner*—José G. Dees
*Assistant Examiner*—Samuel Barts
*Attorney, Agent, or Firm*—Oblon, Spivak, McClelland, Maier & Neustadt

[57] ABSTRACT

Disclosed herein is a method for inhibiting polymerizable (meth)acrylic acid and esters thereof from polymerizing during their production, transportation and storage by using as the inhibitor N-oxyl compound and more than one compound selected from the group consisting of manganese salt compound, copper salt compound, 2,2,6,6,-tetramethylpiperidine compound and nitroso compound. The N-oxyl compound is one or more kinds selected from 2,2,6,6,-tetramethylpiperidinooxyl, 4-hydroxy-2,2,6,6,-tetramethylpiperidinooxyl and 4,4',4"-tris-(2,2,6,6,-tetramethylpiperidinooxyl)phosphite. The combined use of the inhibitors provides superior inhibiting effect to use alone.

2 Claims, No Drawings

METHOD FOR INHIBITING POLYMERIZATION OF (METH) ACRYLIC ACID AND ESTERS THEREOF

BACKGROUND OF THE INVENTION

1. Field of the Invention

The present invention relates to a method for inhibiting the polymerization of (meth)acrylic acid monomers and (meth)acrylate monomers (referred to as (meth)acrylic acid and esters thereof hereinafter).

2. Description of the Prior Art

It is well-known that (meth)acrylic acid and esters thereof have a strong tendency to spontaneous polymerization by light or heat. Hence, it is common practice to add one inhibitor or more in combination to inhibit polymerization during their storage.

An example of the inhibitors which have so far been tried is N-oxyl compound which has N-oxyradicals, such as di-tert-butyl nitroxide and 2,2,6,6,-tetramethyl-4-hydroxypiperidinooxyl( 2,2,6,6-tetramethyl-4-hydroxypiperidine-1-oxyl), as disclosed in British Patent No. 1,127,127. According to the disclosure, they are more effective than known inhibitors such as hydroquinone, phenothiazine, and cupric chloride, when they are used alone. The N-oxyl compound is also used as an inhibitor in the production of methacrylic acid from methacrolein by the aid of an oxygen-containing gas in an organic solvent. It includes 2,2,6,6-tetramethyl-4-hydroxypiperidinooxyl and 2,2,6,6-tetramethylpiperidinooxyl as disclosed in U.S. Pat. No. 4,127,603.

It also includes 2,2,5,5-tetramethyl-3-oxopyrrolidinooxyl and 2,2,6,6-tetramethyl-4-acetoxypiperidinooxyl as disclosed in Japanese Patent Publication No. 46496/1983. In addition, it is shown in Chinese Patent Laid-Open No. 1,052,847A that 2,2,6,6-tetramethyl-4-hydroxypiperidinooxyl effectively inhibits the polymerization of acrylic acid and acrylate when used alone or in combination with hydroquinone.

Contrary to the foregoing, the present inventors have found that the N-oxyl compound used alone or in combination with hydroquinone does not work satisfactorily under specific conditions. In other words, the above-mentioned inhibitor used in an ordinary amount does not work in the production of (meth)acrylic acid by catalytic gas phase reaction, because polymerization of (meth)acrylic acid easily occurs while it is separated by azeotropic distillation from its aqueous solution containing acetic acid and aldehydes. Thus, there was a problem of the formation of popcorn polymers and sticky polymers in the distillation column during distillation, which prevents the continuous operation of the plant for a long period of time. Since large amount of inhibitor was required to obtain effective inhibition, they didn't adapt for practical use.

SUMMARY OF THE INVENTION

It is an object of the present invention to provide a method for inhibiting the polymerization of (meth)acrylic acid and esters thereof with small amount of inhibitor in the above-mentioned process.

The gist of the present invention resides in a method for inhibiting the polymerization of (meth)acrylic acid and esters thereof, the method comprising using, as the inhibitor of the polymerization, N-oxyl compound and more than one compound selected from the group consisting of manganese salt compound, copper salt compound, 2,2,6,6,-tetramethylpiperidine compound and nitroso compound. According to the more desirable embodiment of the present invention, the N-oxyl compound is one or more than one kinds selected from 2,2,6,6,-tetramethylpiperidinooxyl, 4-hydroxy-2,2,6,6,-tetramethylpiperidinooxyl, and 4,4',4"-tris( 2,2,6,6,-tetramethylpiperidinooxyl)phosphite.

DESCRIPTION OF THE PREFERRED EMBODIMENTS

The present inventors researched a series of methods for inhibiting polymerization of (meth)acrylic acid and esters thereof and already filed applications for the method of using a specific N-oxyl compound with phenol compound and phenothiazine compound in combination as inhibitors. (U.S. patent application Ser. No. 08/099,318 which has been allowed with U.S. Pat. No. 5,322,960). Then the inventors have invented another surprisingly effective method for inhibiting polymerization.

The essential prerequisite of the present invention resides in using, as the inhibitor, above-mentioned N-oxyl compound and more than one compound selected from the group consisting of manganese salt compound, copper salt compound, 2,2,6,6,-tetramethylpiperidine compound and nitroso compound. Each compound can be used as an inhibitor by itself, but not show sufficient effect.

The present inventors have found that only when used together with N-oxyl compound, these compounds provide a remarkable synergistic effect for inhibiting the polymerization of (meth)acrylic acid and esters thereof, which they incompletely provide when used alone. The present invention is based on this finding.

The present invention is described in detail hereinafter.

In the present invention, N-oxyl compound is used as an essential component of the inhibitor.

There are no specific restriction on the N-oxyl compound used in the present invention. It is preferred to use one or more than one kinds selected from 2,2,6,6-tetramethylpiperidinooxyl, 4-hydroxy-2,2,6,6-tetramethylpiperidinooxyl, and 4,4',4"-tris-( 2,2,6,6-tetramethylpiperidinooxyl)phosphite.

In the present invention, the four compounds, manganese salt compound, copper salt compound, 2,2,6,6,-tetramethylpiperidine compound and nitroso compound are selected in order to provide an excellent inhibiting effect in combination with N-oxyl compound, and one of these is to be used with N-oxyl compound. Of course, more than one kinds of them may be used together with N-oxyl compound and such an inhibitor using more than three kinds of the compounds provides the similar or more excellent inhibiting effect.

The manganese salt compound used in the present invention may include, for example, manganese di-alkyldithiocarbonate(the alkyl groups are selected from methyl, ethyl, propyl and butyl and may be same or different with each other), manganese diphenyldithiocarbamate, manganese formate, manganese acetate, manganese octanate, manganese naphthenate, potassium permanganate, manganese ehtylendiaminetetraacetate, and the like. One or more kinds of them may be used. The manganese salt compound shows relatively inferior inhibiting effect when it is used alone, however, in using with N-oxyl compound or with N-oxyl compound and other inhibitors as this present invention, it provides an excellent inhibiting effect.

The copper salt compound used in the present invention may include, for example, copper dialkyldithiocarbamate (the alkyl groups are selected from methyl, ethyl, propyl or butyl and may be same or different with each other), copper diphenyldithiocarbamate and the like, and two or more kinds may be used together.

The 2,2,6,6,-tetramethylpiperidine compound used in the present invention may include, for example, 2,2,6,6,6-tetramethylpiperidine, 4-hydroxy-2,2,6,6-tetramethylpiperidine, 1-hydroxy-2,2,6,6,-tetramethylpiperidine, 1,4-dihydroxy-2, 2,6,6,-tetramethylpiperidine and the like, and one or more of them may be used.

The nitroso compound used in the present invention may include, for example, p-nitrosophenol, N-nitrosodiphenylamine, ammonium salt of N-nitrosophenylhydroxyamine and the like, and two or more kinds may be used together.

According to the present invention, the above-mentioned at least two compounds, N-oxyl compound and more than one compound selected from the group consisting of manganese salt compound, copper salt compound, 2,2,6,6,-tetramethylpiperidine compound and nitroso compound produce a pronounced inhibiting effect. Further, other known inhibitors may be used together with the above compounds.

Such known inhibitors may include, for example, hydroquinone, p-methoxyphenol(methoquinone), cresol, t-butylcatechol, diphenyl-amine, phenothiazin, tetraalkylthiuramdisulfide (the alkyl groups mean the same as the above), Methylene Blue and the like. If necessary, they may also be used in combination with molecular oxygen to enhance the inhibiting effect and to provide the continuous operation of the plant for a long period of time.

The inhibiting method of the present invention may be favorably applied to (meth)acrylic acid and esters thereof which are particularly liable to polymerize among vinyl compounds. Examples of the acrylic ester include methyl acrylate, ethyl acrylate, butyl acrylate, 2-ethylhexyl acrylate, 2-hydroxyethyl acrylate, and 2-hydroxypropyl acrylate. Examples of the methacrylic ester include methyl methacrylate, butyl methacrylate, 2-hydroxyethyl methacrylate, and 2-hydroxypropyl methacrylate.

According to the inhibiting method of the present invention, the inhibitors are added to (meth)acrylic acid in distillation all processes, such as rectification column, separation column from solvent, separation column from low-boiling fractions such as acetic acid, and stripper of low-boiling acrolein and methacrolein, in the case where (meth)acrylic acid is produced by the catalytic gas phase reaction.

The method of the present invention consists in adding the above-mentioned two or more inhibitors during the above-mentioned processes. The inhibitors may be added in the form of solid or powder or in the form of aqueous solution or solvent solution. The inhibitors may be added all at once (in the form of solution for example) or one after another. If the inhibitor is to be added during the distillation process in the production of (meth)acrylic acid, it may be dissolved in the feed or reflux.

The amount of the inhibitors to be used is not specifically limited, depending on the operating conditions. Usually, it may be 3–650 ppm (by weight) of the amount of evaporated monomer (or (meth)acrylic acid and esters thereof). The preferred amount of the individual inhibitors of the amount of evaporated monomer is as follows:

N-oxyl compound: 1–100 ppm
Manganese salt compound: 1–50 ppm
Copper salt compound: 1–50 ppm
2,2,6,6,-tetramethylpiperidine compound : 1–500 ppm
Nitroso compound: 1–500 ppm The amount of evaporated monomer means the total amount of monomer vapor which is generated in the reboiler in proportion to the amount of heat fed to the reboiler. The total amount of the monomer vapor can be easily calculated and the calculated numeral is an important factor to determine the amount of the inhibitors to be added.

The optional molecular oxygen may be added to (meth)acrylic acid and esters thereof directly by bubbling or indirectly by dissolution in solvents. Bubbling may be easily accomplished by introducing oxygen gas to the distillation column or stripper from their bottom and/or from the reboiler. The amount of molecular oxygen should preferably be 0.1–1.0 vol % of the amount of evaporated monomer.

Thus the method of the present invention provides the uninterrupted operation of the plant for a long period and stable transportation and storage of (meth)acrylic acid and esters thereof.

EXAMPLES

To further illustrate the invention, and not by way of limitation, the following examples are given. (Unit ppm in the following examples and comparative examples is based by weight)

EXAMPLE 1

Pure acrylic acid was prepared from commercial one by distillation to remove inhibitors. 2 ml each of the pure acrylic acid was placed in a test tube and incorporated with inhibitors in the compositions and the amounts as shown in Table 1 and 2. (The amounts are shown by ppm in the tables hereinafter.) Experiments Nos. 1–10 are for comparison. The test tube was kept reducing pressure and immersed in an oil bath at 100° C.

The time till starting white tubidity by the polymerized products (induction period) was measured by visual inspection. The results are shown in Table 1 and 2. Compounds are abbreviated as follow hereinafter.
PO: 2,2,6,6-tetramethylpiperidinooxyl
4H-PO: 4-hydroxy-2,2,6,6-tetramethylpiperidinooxyl
T-PO: 4,4',4"-tris-(2,2,6,6-tetramethylpiperidinooxy-1)phosphite
MnAc: manganese acetate
CB: copper dibutyldithiocarbamate
4HTMP: 4-hydroxy-2,2,6,6,-tetramethylpiperidine
DHTMP: 1,4-dihydroxy-2,2,6,6,-tetramethylpiperidine
PNP: p-nitrosophenol
NNDPA: N-nitrosodiphenylamine
NPH: ammonium salt of N-nitrosophenylhydroxyamine

TABLE 1

| Run No. | N-oxyl compound | | Mn salt compound | | Cu salt compound | | Piperizine compound | | Nitroso compound | | Induction period (min) |
|---|---|---|---|---|---|---|---|---|---|---|---|
| 1  | 4H-PO | 5  |      |    |    |    |       |    |       |    | 19 |
| 2  | 4H-PO | 10 |      |    |    |    |       |    |       |    | 36 |
| 3  |       |    | MnAc | 5  |    |    |       |    |       |    | 5 |
| 4  |       |    | MnAc | 10 |    |    |       |    |       |    | 5 |
| 5  |       |    |      |    | CB | 5  |       |    |       |    | 10 |
| 6  |       |    |      |    | CB | 10 |       |    |       |    | 18 |
| 7  |       |    |      |    |    |    | DHTMP | 5  |       |    | 6 |
| 8  |       |    |      |    |    |    | DHTMP | 10 |       |    | 7 |
| 9  |       |    |      |    |    |    |       |    | NNDPA | 5  | 7 |
| 10 |       |    |      |    |    |    |       |    | NNDPA | 10 | 8 |
| 11 | 4H-PO | 5  | MnAc | 5  |    |    |       |    |       |    | >240 |
| 12 | PO    | 5  | MnAc | 5  |    |    |       |    |       |    | >240 |
| 13 | T-PO  | 5  | MnAc | 5  |    |    |       |    |       |    | >240 |
| 14 | 4H-PO | 5  |      |    | CB | 5  |       |    |       |    | 110 |
| 15 | 4H-PO | 5  |      |    |    |    | DHTMP | 5  |       |    | 103 |
| 16 | 4H-PO | 5  |      |    |    |    | 4HTMP | 5  |       |    | 101 |
| 17 | 4H-Po | 5  |      |    |    |    |       |    | NNDPA | 5  | 128 |
| 18 | 4H-PO | 5  |      |    |    |    |       |    | PNP   | 5  | 115 |
| 19 | 4H-PO | 5  |      |    |    |    |       |    | NPH   | 5  | 103 |
| 20 | 4H-PO | 4  | MnAc | 3  | CB | 3  |       |    |       |    | >240 |
| 21 | 4H-PO | 4  | MnAc | 3  |    |    | DHTMP | 3  |       |    | >240 |
| 22 | 4H-PO | 4  | MnAc | 3  |    |    |       |    | NNDPA | 3  | >240 |
| 23 | 4H-PO | 3  | MnAc | 3  | CB | 2  | DHTMP | 2  |       |    | 210 |
| 24 | 4H-PO | 3  | MnAc | 3  | CB | 2  |       |    | NNDPA | 2  | 230 |
| 25 | 4H-PO | 2  | MnAc | 2  | CB | 2  | DHTMP | 2  | NNDPA | 2  | 190 |
| 26 | 4H-PO | 4  |      |    | CB | 3  | DHTMP | 3  |       |    | 101 |
| 27 | 4H-PO | 4  |      |    | CB | 3  |       |    | NNDPA | 3  | 105 |
| 28 | 4H-PO | 3  |      |    | CB | 3  | DHTMP | 2  | NNDPA | 2  | 92 |
| 29 | 4H-PO | 4  |      |    |    |    | DHTMP | 3  | NNDPA | 3  | 125 |

TABLE 2

| Run No. | N-oxyl compound | | Mn salt compound | | Hydro-quinone | Metho-quinone | Pheno-thiazine | Induction period (min) |
|---|---|---|---|---|---|---|---|---|
| 30 | 4H-PO | 4 | MnAc | 3 | 3 |   |   | >240 |
| 31 | 4H-PO | 4 | MnAc | 3 |   | 3 |   | >240 |
| 32 | 4H-PO | 4 | MnAc | 3 |   |   | 3 | >240 |
| 33 | 4H-PO | 3 | MnAc | 3 | 2 |   | 2 | 180 |
| 34 | 4H-PO | 3 | MnAc | 3 |   | 2 | 2 | 200 |

From Table 1, it is clear that the inhibiting effect is inferior in comparison experiments Nos. 1–10 where the inhibitor was used alone, to the present invention experiments Nos. 11–29 where 2–5 inhibitors were used together, since the comparison examples showed shorter induction period. Though the total amount (100 ppm) of the used inhibitors of the present invention was same as that of comparison Examples Nos. 2,4,6,8 and 10 in which inhibitors were used alone, there seems a large difference concerning their induction period. Thus synergistic effect by using inhibitors in plural clearly appears. Especially in using manganese salt compound with N-oxyl compound, the synergistic effect is significant.

Additionally, from Table 2, it is clear that similar inhibiting effect was obtained when other known inhibitors were used (Examples Nos. 30–34) adding to the inhibitors in pair defined in this invention (Example No. 11).

EXAMPLE 2

The inhibiting effect was evaluated in azeotropic separation of acrylic acid from its aqueous solution (containing 30 wt % water and 2.5 wt % acetic acid) resulting from the catalytic gas phase reaction of propylene. The azeotropic separation was carried out using a packed column with a feed pipe in the middle and a condenser at the top and also using methyl isobutyl ketone as reflux, with the pressure being 160 mmHg and the temperature being 49° C. at the top and 97° C. at the bottom. Each of the inhibitors shown in Table 3 was added to the reflux (which was fed to the column) and oxygen gas was fed to the bottom of the column. The amounts of the inhibitors and oxygen are based on the amount of evaporated acrylic acid. It was found that the bottom product in the steady state was composed of 97 wt % acrylic acid and 0.5 wt % acetic acid, with the remainder being 2.5 wt %. After continued operation for 8 hours, with recycled oil phase as the reflux, the amount of polymers formed in the column was determined through suction drying to obtain constant weight. The results are shown in Table 3.

TABLE 3

| Run | Inhibitors (ppm) | | | | | Amount of oxygen | Amount of polymer |
|---|---|---|---|---|---|---|---|
| No. | 4H-PO | MnAc | CB | DHTMP | NNDPA | (vol %) | formed (g) |
| 35 | 3.3 |  |  |  |  | 0.21 | 10.4 |
| 36 |  | 3.3 |  |  |  | 0.21 | 53.8 |
| 37 |  |  | 3.3 |  |  | 0.21 | 41.8 |
| 38 |  |  |  | 3.3 |  | 0.21 | 38.5 |
| 39 |  |  |  |  | 3.3 | 0.21 | 25.1 |
| 40 | 3.3 | 3.3 |  |  |  | 0.21 | 1.2 |
| 41 | 3.3 |  | 3.3 |  |  | 0.21 | 2.5 |
| 42 | 3.3 |  |  | 3.3 |  | 0.21 | 2.3 |
| 43 | 3.3 |  |  |  | 3.3 | 0.21 | 1.9 |

From Table 3, it is clear that the amount of the formed polymer was very small in experiments Nos. 40–43 (pertaining to present invention) and that the inhibitor of the present invention performs an excellent effect.

EXAMPLE 3

Pure methacrylic acid was prepared from commercial one by distillation to remove inhibitors. 2 ml each of pure methacrylic acid was placed in a test tube and incorporated with inhibitors in the compositions and the amounts as shown in Table 4. Experiments Nos. 44–48 are for comparison. The test tube was kept reducing pressure and immersed in an oil bath at 130° C.

Induction period was measured by visual inspection. The results are shown in Table 4.

TABLE 4

| Run | Inhibitors (ppm) | | | | | Induction period |
|---|---|---|---|---|---|---|
| No. | 4H-PO | MnAc | CB | DHTMP | NNDPA | (min) |
| 44 | 10 |  |  |  |  | 65 |
| 45 |  | 10 |  |  |  | 7 |
| 46 |  |  | 10 |  |  | 19 |
| 47 |  |  |  | 10 |  | 8 |
| 48 |  |  |  |  | 10 | 25 |
| 49 | 5 | 5 |  |  |  | >240 |
| 50 | 5 |  | 5 |  |  | >240 |
| 51 | 5 |  |  | 5 |  | >240 |
| 52 | 5 |  |  |  | 5 | >240 |
| 53 | 4 | 3 | 3 |  |  | >240 |
| 54 | 4 | 3 |  | 3 |  | >240 |
| 55 | 4 | 3 |  |  | 3 | >240 |
| 56 | 3 | 3 | 2 | 2 |  | >240 |
| 57 | 3 | 3 |  | 2 | 2 | >240 |
| 58 | 2 | 2 | 2 | 2 | 2 | 220 |
| 59 | 4 |  | 3 | 3 |  | >240 |
| 60 | 4 |  | 3 |  | 3 | >240 |
| 61 | 3 |  | 3 | 2 | 2 | >240 |
| 62 | 4 |  |  | 3 | 3 | >240 |

From Table 4, it is clear that Examples Nos. 49–62 showed a synergistic inhibiting effect of the present invention, since they showed longer induction period though the used amount of the inhibitors was same as that of comparison Examples Nos. 44–48.

EXAMPLE 4

Four pure acrylates (methyl acrylate (AM), ethyl acrylate (AE), butyl acrylate (AB), and octyl acrylate (AO)) were prepared from commercial ones by distillation to remove inhibitors. 30 ml each of the pure acrylate was placed in a test tube and incorporated with inhibitors in the compositions and the amounts as shown in Table 5. The test tube was kept reducing pressure and immersed in an oil bath at 70° C. for AM, 90° C. for AE, and 120° C. for AB and AO. The time till starting heat polymerization generation was measured as induction period. The results are shown in Table 5.

TABLE 5

| Run | Inhibitors (ppm) | | | | | Induction period (min) | | | |
|---|---|---|---|---|---|---|---|---|---|
| No. | 4H-PO | MnAc | CB | DHTMP | NNDPA | AM | AE | AB | AO |
| 63 | 10 |  |  |  |  | 55.0 | 50.5 | 35.5 | 100.5 |
| 64 |  | 10 |  |  |  | 5.5 | 5.0 | 4.0 | 15.5 |
| 65 |  |  | 10 |  |  | 11.5 | 10.5 | 8.5 | 25.0 |
| 66 |  |  |  | 10 |  | 6.0 | 5.5 | 7.0 | 14.5 |
| 67 |  |  |  |  | 10 | 48.0 | 44.5 | 30.5 | 77.5 |
| 68 | 5 | 5 |  |  |  | >240 | >240 | >240 | >240 |

TABLE 5-continued

| Run | Inhibitors (ppm) | | | | | Induction period (min) | | | |
|---|---|---|---|---|---|---|---|---|---|
| No. | 4H-PO | MnAc | CB | DHTMP | NNDPA | AM | AE | AB | AO |
| 69 | 5 | | 5 | | | >240 | >240 | >240 | >240 |
| 70 | 5 | | | 5 | | >240 | >240 | >240 | >240 |
| 71 | 5 | | | | 5 | >240 | >240 | >240 | >240 |

From Table 5, it is clear that Examples Nos. 68–71 where inhibitors were used in pairs showed an excellent inhibiting effect of the present invention for any of the acrylate.

EXAMPLE 5

Two pure methacrylates (methyl methacrylate (MMA) and butyl methacrylate (BMA)) were prepared from commercial ones by distillation to remove inhibitors. 30 ml each of the pure methacrylate was placed in a test tube and incorporated with inhibitors in different compositions and amounts as shown in Table 6. The test tube was kept reducing pressure and immersed in an oil bath at 90° C. for MMA and 120° C. for BMA.

Induction period was measured in the same manner as in Example 4. The results are shown in Table 6.

EXAMPLE 6

Four pure (meth)acrylates (listed below) were prepared from commercial ones by distillation to remove inhibitors. 30 ml each of the pure (meth)acrylate was placed in a test tube and incorporated with inhibitors in the amounts as shown in Table 7. The test tube was kept reducing pressure and immersed in an oil bath at 100° C.

The time till starting heat polymerization generation was measured as induction period. The results are shown in Table 7.
HEA: 2-hydroxyethyl acrylate
HPA: 2-hydroxypropyl acrylate
HEMA: 2-hydroxyethyl methacrylate
HPMA: 2-hydroxypropyl methacrylate

TABLE 6

| Run | Inhibitors (ppm) | | | | | Induction period (hr) | |
|---|---|---|---|---|---|---|---|
| No. | 4H-PO | MnAc | CB | DHTMP | NNDPA | MMA | BMA |
| 72 | 10 | | | | | 62.0 | 33.5 |
| 73 | | 10 | | | | 2.5 | 1.5 |
| 74 | | | 10 | | | 7.0 | 6.0 |
| 75 | | | | 10 | | 7.5 | 5.5 |
| 76 | | | | | 10 | 55.0 | 21.0 |
| 77 | 5 | 5 | | | | >240 | >240 |
| 78 | 5 | | 5 | | | >240 | >240 |
| 79 | 5 | | | 5 | | >240 | >240 |
| 80 | 5 | | | | 5 | >240 | >240 |

From Table 6, it is clear that Examples Nos. 77–80 (pertaining to the present invention) where the inhibitors were used in pairs shows an excellent inhibiting effect against any of the methacrylate.

TABLE 7

| Run | Inhibitors (ppm) | | | | | Induction period (min) | | | |
|---|---|---|---|---|---|---|---|---|---|
| No. | 4H-PO | MnAc | CB | DHTMP | NNDPA | HEA | HPA | HEMA | HPMA |
| 81 | 10 | | | | | 89.5 | 210.0 | 152.0 | 98.5 |
| 82 | | 10 | | | | 1.5 | 10.0 | 7.5 | 5.5 |
| 83 | | | 10 | | | 10.0 | 19.5 | 15.0 | 11.0 |
| 84 | | | | 10 | | 2.5 | 15.5 | 10.5 | 9.0 |
| 85 | | | | | 10 | 71.0 | 134.5 | 99.5 | 68.0 |
| 86 | 5 | 5 | | | | >480 | >480 | >480 | >480 |
| 87 | 5 | | 5 | | | >480 | >480 | >480 | >480 |
| 88 | 5 | | | 5 | | >480 | >480 | >480 | >480 |
| 89 | 5 | | | | 5 | >480 | >480 | >480 | >480 |

From Table 7, it is clear that the inhibiting effect in the present invention is excellent.
Effect of Invention The method for inhibiting polymerization of the present invention has been described above. It consists of as the inhibitor using N-oxyl compound and more than one compound selected from the group consisting of manganese salt compound, copper salt compound. 2,2,6,6-tetramethylpiperidine compound and nitroso compound. The combinated use of the above inhibitors provides superior inhibiting effect to use alone. It has now become possible to prevent (meth)acrylic acid and esters thereof from polymerizing even under the condition that occurs their polymerization very easily. Thus the method of the present invention provides the uninterrupted operation of the plant for a long period and stable transportation and storage of (meth)acrylic acid and esters thereof.

What is claimed is:

1. A method for inhibiting the polymerization of (meth)acrylic acid and esters thereof, said method comprising using as the inhibitor N-oxyl compound and more than one compound selected from the group consisting of manganese salt compound, copper salt compound, 2,2,6,6,-tetramethylpiperidine compound and nitroso compound.

2. A method for inhibiting polymerization as defined in claim 1, wherein the N-oxyl compound is one or more kinds selected from 2,2,6,6,-tetramethylpiperidinooxyl, 4-hydroxy-(2,2,6,6,-tetramethylpiperidinooxyl and 4,4',4"-tris-(2,2,6,6,-tetramethylpiperidinooxyl)phosphite.

* * * * *